United States Patent [19]

Smith

[11] Patent Number: 4,960,567

[45] Date of Patent: Oct. 2, 1990

[54] APPARATUS FOR ANALYZING FLUID INCLUSIONS

[75] Inventor: Michael P. Smith, Tulsa, Okla.

[73] Assignee: Amoco Corporation, Chicago, Ill.

[21] Appl. No.: 394,350

[22] Filed: Aug. 15, 1989

Related U.S. Application Data

[63] Continuation of Ser. No. 51,555, May 18, 1987, Pat. No. 4,898,831.

[51] Int. Cl.$^5$ .............................................. G01N 7/00
[52] U.S. Cl. ........................................ 422/83; 422/78
[58] Field of Search .................... 436/32, 807; 422/68, 422/78, 80, 83, 99, 63

[56] References Cited

PUBLICATIONS

"Mass Spectrometric Determination of Gases in Individual Fluid Inclusions . . . " Barker et al., *Anal. Chem.*, 1986, 58, 1330–1333.
"The Analysis of Fluid Inclusions in Halite" Lazar et al., *Geochimica Cosmochimica Acta*, vol. 52, pp. 485–490, 1988.
"Chemical Composition of Liquid Inclusions in Icelandic Spar and Genetic Problems", Khitarov et al., *Geochem.*, No. 3, pp. 269–278, 1958.
"Liquid Inclusions in Minerals as a Geologic Barometer" Kalyuzhnyy, *International Geology Review*, pp. 181–195.

*Primary Examiner*—Robert A. Wax
*Assistant Examiner*—T. J. Wallen

[57] ABSTRACT

Apparatus for analyzing fluid inclusions. A sectioned mineral sample is mounted on a glass slide and placed in a vacuum chamber. An optical microscope is used to examine the sample through a window in the vacuum chamber to identify a single fluid inclusion. A linear rotary feedthrough includes a diamond stylus on the end thereof that is received in the vacuum chamber. The feedthrough is manipulated by the operator to urge the diamond stylus against the identified fluid inclusion thereby rupturing the same. The gases, including evaporated volatile liquids, released from the inclusion are analyzed by a mass spectrometer.

5 Claims, 5 Drawing Sheets

APPARATUS FOR ANALYZING FLUID INCLUSIONS

This is a continuation of copending application Ser. No. 051,555 filed May 18, 1987, now U.S. Pat. No. 4,898,831.

BACKGROUND OF THE INVENTION

1. Field of the Invention

The instant invention relates to methods and apparatus for analyzing fluid inclusions and more particularly to such methods and apparatus in which a fluid inclusion formed in a material such as mineral, glass, semiconducting material, and the like is ruptured, and the gases released therefrom are analyzed.

2. Setting of the Invention

When natural minerals are formed, fluid present in the vicinity of the crystal may be trapped in microscopic defects known as fluid inclusions. These fluid inclusions may be ruptured to release the paleofluids contained therein in order to analyze the same. Such analysis can be used to determine information relating to the nature of the fluids present when the mineral was formed.

Analysis of fluid inclusions formed in sedimentary environments can yield information which is useful in the exploration for and production of oil and gas. For example, such studies can produce information relating to timing of hydrocarbon migration relative to rock formation, pathways of hydrocarbon migration, and the influence of hydrocarbons on rock formation.

Fluid inclusions in minerals may be formed at the time of mineral growth or they may form later when cracks in the mineral heal. Fluid inclusions formed at the time of initial mineral growth are referred to as primary inclusions, and those formed during healing of cracks in the already-formed mineral are known as secondary inclusions. Cracks which have formed and healed at different times in the mineral's past produce different generations of secondary inclusions which trap environmental fluids present at the time of healing of the crack.

Sometimes a mineral overgrowth which acts as a cement may form between and around previously-formed mineral growth. Environmental fluids may also be trapped in fluid inclusions formed in the cement.

In the past, a number of different techniques have been utilized to release fluids from the inclusions in minerals and in other substances, such as glass. Such techniques include crushing and drilling. In another technique, the material, for example, a naturally-occurring mineral, is heated thereby increasing the fluid pressure in the fluid inclusions until the same rupture thereby releasing the fluids. This technique is known in the art as thermal decrepitation. A related technique involves use of a laser beam. When the laser beam is directed toward an area of interest in the mineral, the fluids in the inclusions are heated thereby rupturing the inclusion and releasing the fluids.

In the past, mass spectrometers have been used to analyze gases released from fluid inclusions using one of the above-described prior art techniques. Typically, the gases are released by cutting or crushing the mineral or by thermal decrepitation. Whatever the technique for releasing the gas, the gases are released into a vacuum which is in communication with the mass spectrometer. When the fluids are released from the inclusions into the vacuum, the volatile liquids in the inclusions evaporate. The gases are provided directly to the mass spectrometer where they are ionized and thereafter qualitatively and/or quantitatively analyzed in the usual manner. The mass spectrometer may be used to analyze the chemistry of the gases and evaporated volatile liquids and/or to analyze the isotopic ratios of elements contained therein.

A problem exists with the various prior art methods for releasing fluids from inclusion in naturally-occurring minerals and the like. When utilizing techniques such as crushing, slicing, and drilling, invariably fluids from more than one inclusion are released substantially simultaneously. This is especially true when dealing with small inclusions. For example, fluid inclusions of interest in sedimentary minerals are typically less than 10 microns in diameter. Thus, the analysis undertaken, whether by mass spectroscopy or by other means, may be of a plurality of fluid inclusions. Moreover, the analyzed fluids may be from inclusions formed at vastly differing times, such as a mixture of primary and secondary inclusions or a mixture of different generations of secondary inclusions.

Also, the mineral sample to be analyzed may include a plurality of different minerals closely adjacent one another as well as mineral growth formed between and on the various minerals, all of which include fluid inclusions. When such a sample is crushed, sliced, or drilled, fluids from inclusions in different minerals or from one or more cements may be simultaneously released. Such techniques prevent accurate analysis of selected types of inclusions such as inclusions from a particular mineral or cement or such as only primary inclusions, only secondary inclusions, or only a selected generation of secondary inclusions.

Some theorize that when fluids are released from inclusions in naturally-occurring minerals by thermal decrepitation, single inclusions sequentially burst in response to increasing temperature. However, there is no known way to verify this. Data generated by mass spectroscopy analysis of gases, including evaporated liquids, released from fluid inclusions may be interpreted to mean that (a) only a single inclusion ruptured at a specified temperature or (b) groups of inclusions ruptured at a specified temperature.

Even if it could be verified that only a single inclusion at a time burst as temperature is increased, this technique does not permit selection of a single identified inclusion nor does it permit selection of one inclusion from among a class of characterized inclusions, such as primary inclusions, secondary inclusions, a selected generation of secondary inclusions, inclusions from a selected cement, etc. In other words, as the temperature increases, any of the inclusions in the sample being tested may rupture, and there exists no control over selection of a particular fluid inclusion or a fluid inclusion from among a particular class of inclusions to be ruptured.

The laser technique suffers from similar drawbacks. Typically, a selected area in a mineral sample is located using a microscope. Thereafter, a laser beam is shined through the microscope onto the sample and the heat generated thereby ruptures inclusions in the general area. Although the laser technique allows exercise of greater control over which inclusions are to be ruptured than thermal decrepitation of the entire sample, the heat produced by the laser beam is applied to a general area of the sample, and it is not possible to limit the technique to rupture only a single selected inclusion. Thus, the above-described drawbacks of the thermal decrepitation technique are also present when a laser is used to release gases, including evaporated volatile liquids from fluid inclusions. In addition, the laser heat can also release gases from volatile matter received in cracks in the sample or from adsorbed fluid in the sample. Therefore, at least some of the analyzed gas may be from sources other than fluid inclusions.

There exists a need for a method and apparatus for analyzing fluid inclusions in which a single identified fluid inclusion may be ruptured.

There exists a need for such a method and apparatus in which selected fluid inclusions from an identified class of inclusions may be selectively ruptured.

There exists a further need for such a method and apparatus in which a plurality of identified fluid inclusions may be individually and sequentially mechanically ruptured.

SUMMARY OF THE INVENTION

The method of the invention comprises the steps of characterizing a class of fluid inclusions formed in a naturally-occurring mineral or the like; identifying a single fluid inclusion within the characterized class; mechanically rupturing the identified fluid inclusion; and analyzing the gases released from the fluid inclusion.

In another aspect of the invention, a second fluid inclusion within the characterized class is identified, mechanically ruptured, and the resulting released gases analyzed.

In still another aspect of the method, a fluid inclusion in a sample containing a plurality of minerals is identified and mechanically ruptured and the resulting gases analyzed. Thereafter, a second fluid inclusion formed in a second mineral in the sample is mechanically ruptured and the gases released therefrom analyzed.

In yet another aspect of the invention, apparatus is provided for performing the steps of the method.

Additional advantages associated with the instant invention will become more fully apparent when the following detailed description is read in view of the accompanying drawings, wherein.

DETAILED DESCRIPTION OF THE PREFERRED EMBODIMENTS OF THE INVENTION

Figure 1:
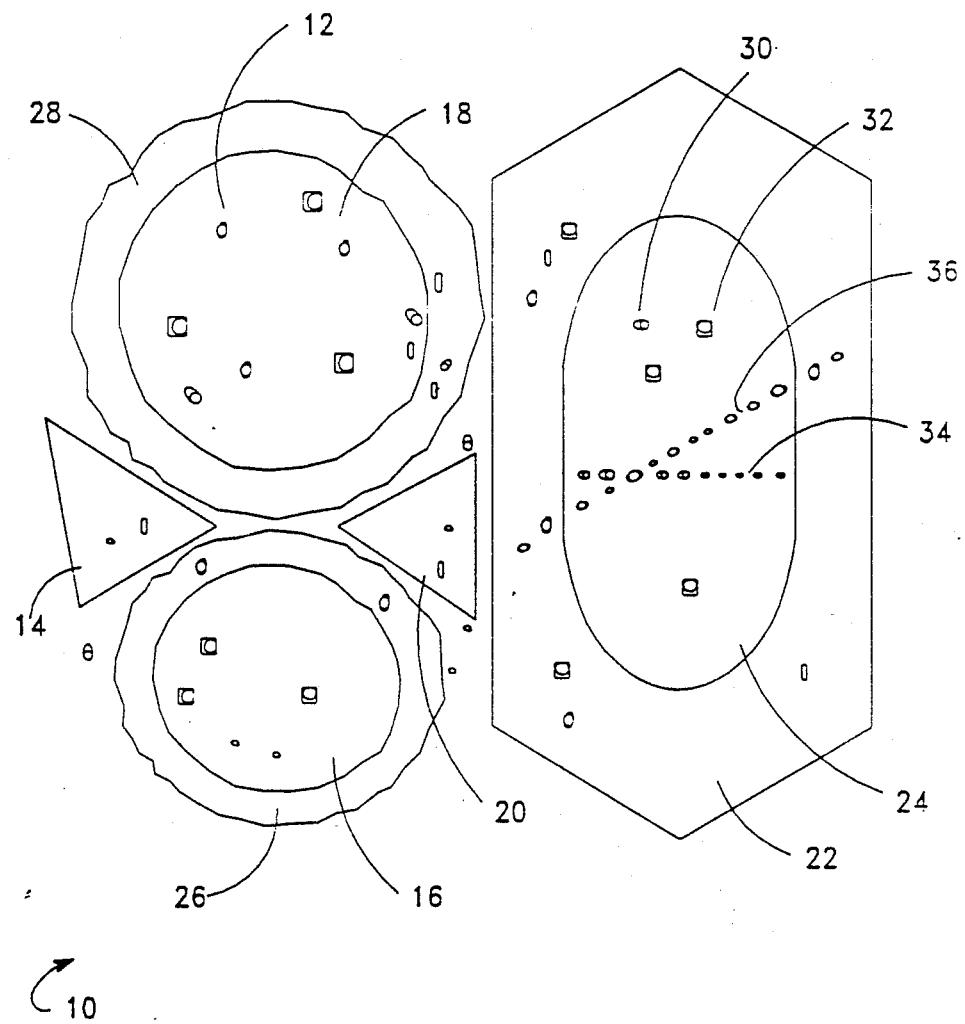
FIG. 1 is an enlarged view of a portion of a sectioned mineral sample containing a plurality of mineral growths as viewed through a microscope.

Turning now to the drawings and particularly to FIG. 1, consideration will now be given to an example of a mineral sample containing a plurality of mineral growths. Indicated generally at 10 is a portion of a sample extracted from naturally-occurring mineral growth. Sample 10 consists of a cut section having a thickness of approximately 0.03–1.0 millimeter which is polished on both sides and which is mounted on a glass slide (not visible in FIG. 1). The view of FIG. 1 is a view of the polished section, as seen through a microscope, and is thus greatly enlarged. The approximate scale can be indicated in that substantially all of the fluid inclusions, like inclusion 12, formed in the various mineral growths in sample 10, are under 10 microns in diameter. Sample 10 includes a plurality of mineral growths, like minerals 14, 16, 18, 10, 22, and 24. Minerals 16 and 18 each include a mineral overgrowth 26 and 28 which acts as and is referred to herein as a cement.

Mineral 24 includes therein a plurality of primary inclusions, like inclusions 30, 32. These inclusions were formed during the initial growth of mineral 24. A healed crack 34 is formed in mineral 24, and a healed crack 36 is formed in mineral 22 and in mineral 24. Crack 34 was formed in mineral 24 after the original growth of mineral 24, and thus after the primary inclusions, like inclusions 30, 32, were formed. Crack 36 was also formed in minerals 22, 24 after the formation of the primary inclusions in both minerals 22, 24. Each of cracks 34, 36 have a plurality of secondary inclusions, as shown, formed therealong. These secondary inclusions were formed during healing of cracks 34, 36 when mineral growth developed in the cracks. It is to be appreciated that the secondary inclusions in crack 34 trap environmental fluids at a later time than the primary inclusions in mineral 24, and the secondary inclusions along crack 36 trap such fluids at a later time than when the environmental fluids were trapped in the primary inclusions in both minerals 22, 24. Moreover, the secondary inclusions in crack 34 may well be formed at a time far removed from those formed in crack 36, and thus the secondary inclusions in crack 34 may be of a different generation than those along crack 36. Likewise, the primary inclusions formed in the various minerals and cements in sample 10 may be formed at vastly different times from one another thus trapping the environmental fluids present at the time of formation.

It should be noted that sample 10 may be taken from a portion of naturally-occurring mineral growth using the usual sawing and polishing techniques. After the sample is cut, polished, and mounted on a slide, the same may be observed through a microscope to obtain the view of FIG. 1. Geologists are able to identify, by observation through the microscope, various types of minerals. Such identification is based on well-known criteria of shape, of mineral growth, and various optical properties. In addition, the fluid inclusions themselves can be classified in different ways such as the above-described primary and secondary fluid inclusions. Other categories of inclusion classifications may be utilized; however, most common is classifying by origin, namely primary and secondary inclusions. Such inclusions may be characterized by observation of the sample through the microscope.

Figure 2:
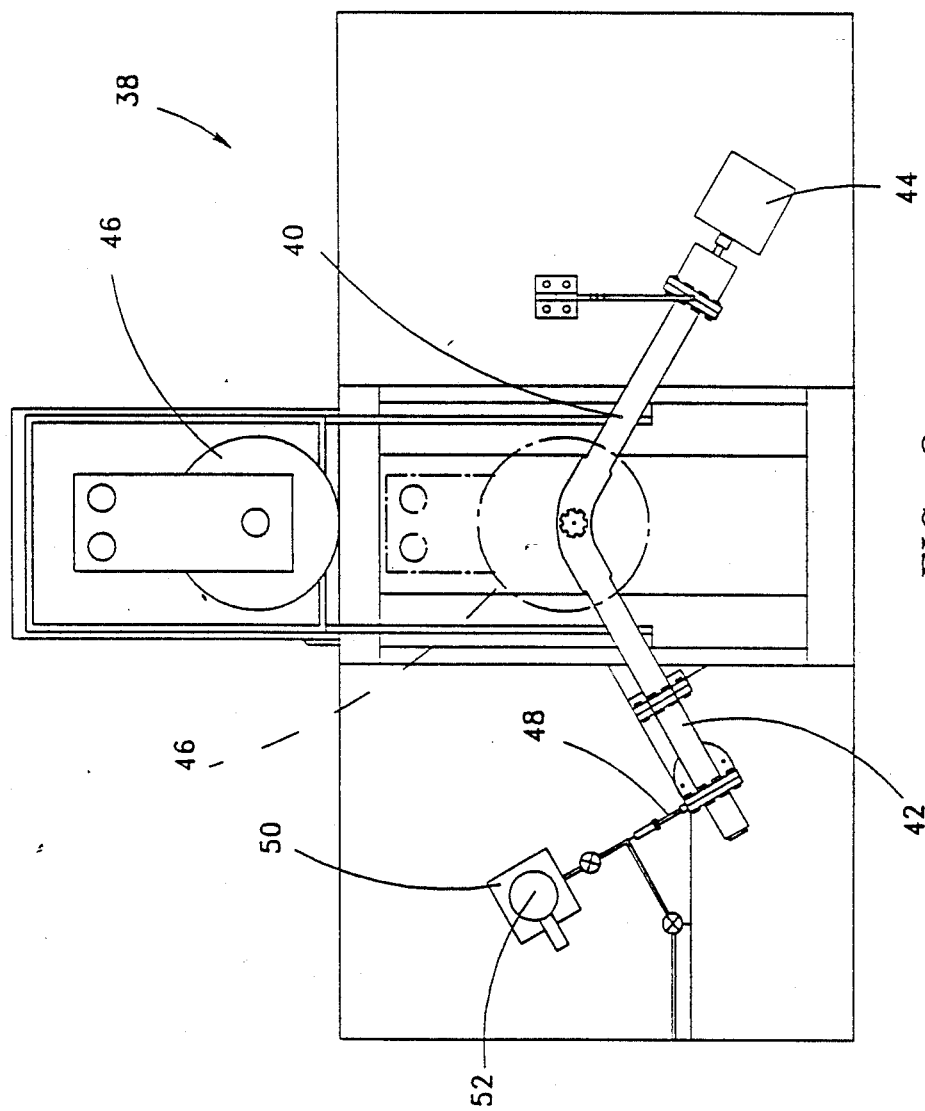
FIG. 2 is a top plan view of apparatus constructed in accordance with the instant invention.
Figure 3:
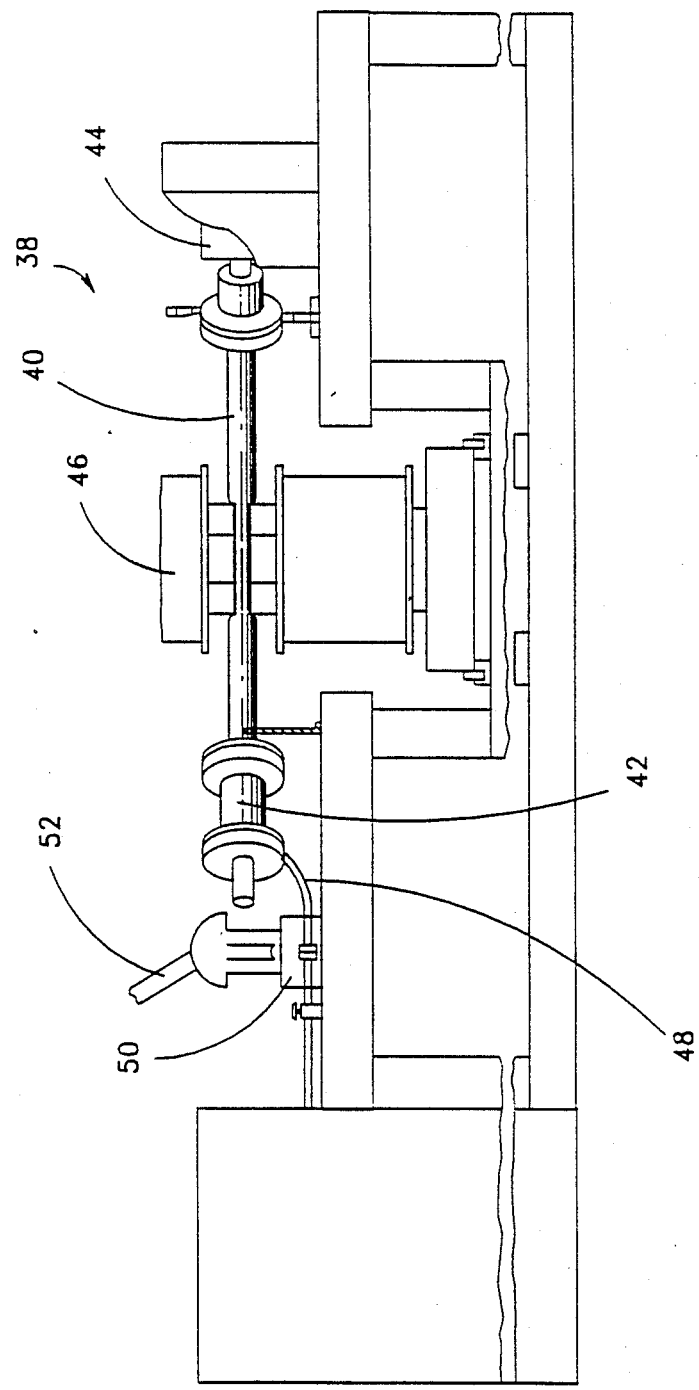
FIG. 3 is a front view of the apparatus shown in FIG. 2.

Turning now to FIGS. 2 and 3, indicated generally at 38 is apparatus constructed in accordance with the instant invention. Included therein is a tube 40 having an ionization chamber 42 mounted on one end thereof, and an ion detector 44 mounted on the other end thereof. A magnet 46 is shown in a solid-line position in FIG. 2 removed to the rear of tube 40 and in a dashed-line position about tube 40. A tube 48 is in communication with ionization chamber 42 and provides a gas sample to the ionization chamber for analysis. In operative condition, a vacuum pump (not shown) maintains a substantial vacuum in tube 40.

That portion of the apparatus shown in FIGS. 2 and 3, which has been described above, comprises a commercially available gas spectrometer, such being also referred to herein as means for analyzing gases. Generally speaking, the gas spectrometer operates as follows:

A gas sample to be analyzed is provided to ionization chamber 42 via tube 48. In the ionization chamber, an electron beam ionizes the gases which are then accelerated by an electric field along tube 40 toward magnet 46. The magnetic field alters the direction of travel of the ions in tube 40 depending upon the electrical charge and mass of each ion and upon the strength of the magnetic field. Ions of a certain mass-to-charge ratio travel around the bend in tube 40 toward detector 44. Other ions strike the walls of tube 40 and are not ultimately detected. The foregoing description of the operation of the mass spectrometer describes in general the operation of commercially available mass spectrometers. Such mass spectrometers may be used to analyze gases present and to analyze isotope ratios of elements in the gases.

A vacuum chamber 50 is in fluid communication with ionization chamber 42 via tube 48. A commercially available microscope 52 is positioned over vacuum chamber 50. For a more detailed view of vacuum chamber 50, attention is directed to FIG. 4.

Chamber 50 is in fluid communication with ionization chamber 42 via tube 48. As mentioned, tube 40 of the mass spectrometer is maintained in a substantial vacuum by a pump (not shown), and thus tube 48 and chamber 50 are also maintained in a vacuum.

Figure 4:
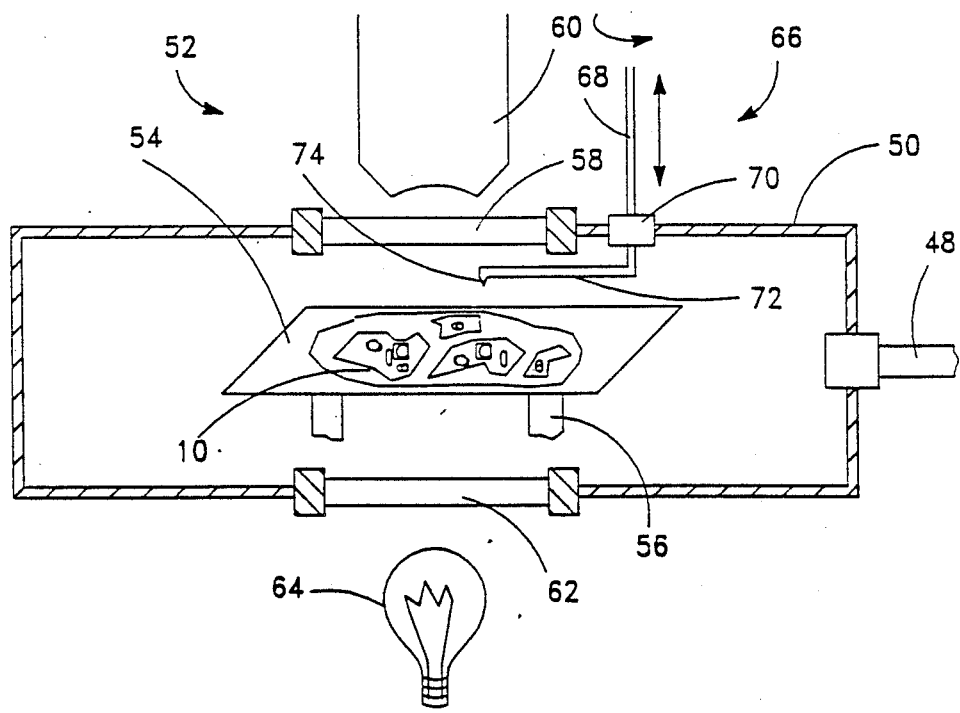
FIG. 4 is an enlarged somewhat schematic view, shown partly in cross-section, of a portion of the apparatus shown in FIGS. 2 and 3.

Sample 10, as will be recalled, is mounted on a glass slide 54 which is viewable in FIG. 4. Slide 54, in the view of FIG. 4, is tilted forward to show sample 10. In operative condition, the slide is substantially parallel to the upper and lower walls of chamber 50. Slide 54 is removably mounted on a commercially available manipulator 56 which enables the slide to be moved laterally and vertically responsive to a commercially available operator control (not shown) for the manipulator. Chamber 50 includes a glass window 58 formed in an upper wall thereof over which is positioned a lower housing 60 of microscope 52. A lower window 62 is formed in a lower wall of vacuum chamber 50 beneath window 58. A light 64 is positioned beneath window 62.

Indicated generally at 66 is a rotary linear feedthrough. Feedthrough 66 includes a shaft 68 which extends through a seal 70. The lower end of the shaft is connected to an arm 72. A diamond stylus 74 is mounted on the end of arm 72 and is positioned so that a point formed thereon is directed downwardly.

Shaft 68, when rotated under operator control, imparts rotary motion to arm 72 about the axis of shaft 68. Also, the operator may raise and lower shaft 68 to effect raising and lowering of arm 72.

Figure 5:
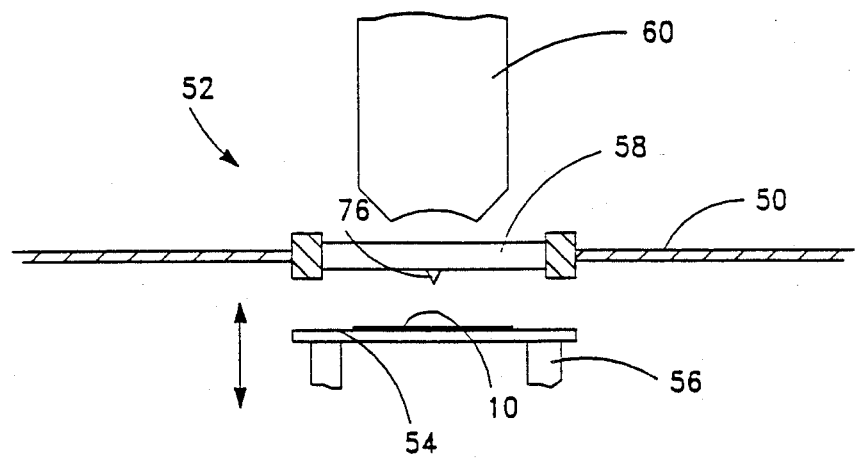
FIG. 5 is a schematic view similar to FIG. 4 of an alternative embodiment of the apparatus of the instant invention.

Attention is next directed to FIG. 5 wherein the structure previously identified with a numeral herein retains the same number in FIG. 5. In the embodiment of FIG. 5, a diamond stylus 76 is mounted directly on the underside at window 58 above sample 10 with a point formed on the stylus being directed downwardly.

Figure 6:
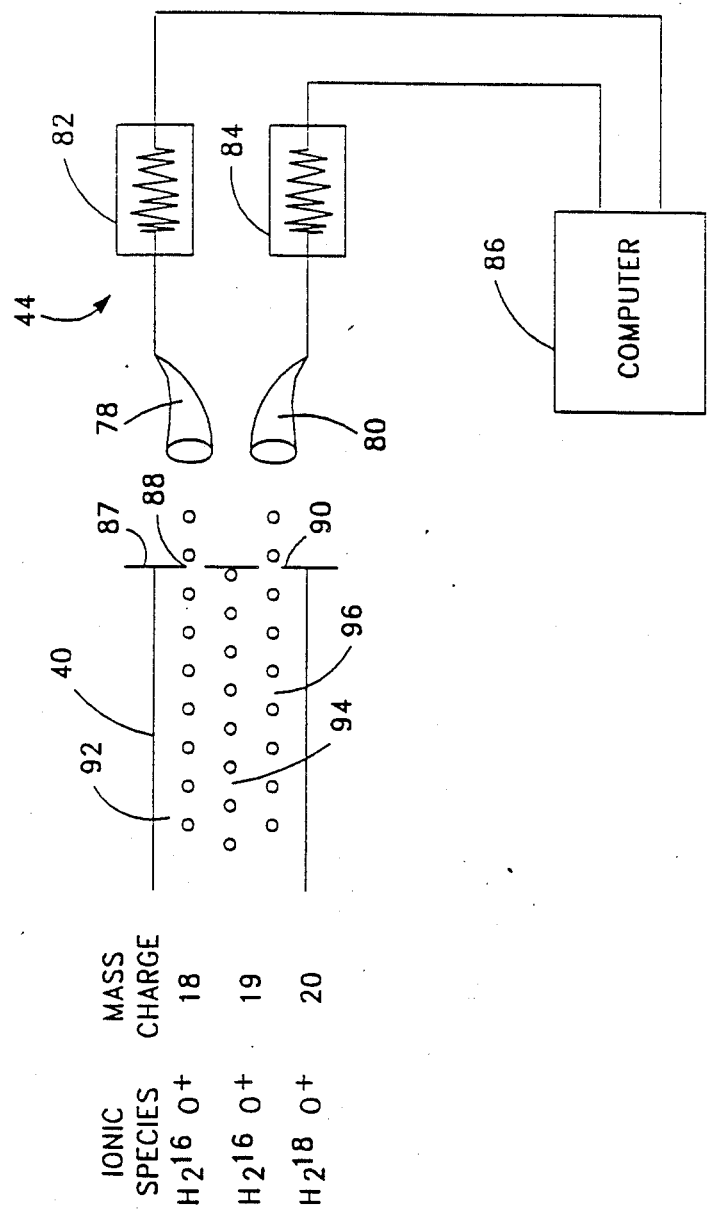
FIG. 6 is a schematic diagram of a portion of the apparatus of FIGS. 2 and 3.

Turning now to FIG. 6, ion detector 44 includes therein a pair of commercially available Gallileo-type electron multipliers 78 and 80. Each of the electron multipliers is connected to an associated ion counter 82, 84 which, in turn, are connected to a commercially available computer 86. The end of tube 40, which is directed toward ion detector 44, includes an end plate 87 having slits, such as slits 88, 90, formed therein. End plate 87 may be fixed in selected positions relative to tube 40, thereby varying the radial position of the slits relative to the longitudinal axis of tube 40.

Consideration will now be given to the operation of the instant embodiments of the invention. When a mineral growth of interest is located, sample 10 is prepared in the usual fashion. A slice is taken from the mineral growth and is thereafter polished and mounted on glass slide 54, as shown in FIGS. 4 and 5. Thereafter, slide 54 is mounted on manipulator 56 and light 64 is turned on. An operator examines sample 10 through microscope 52 and positions the same beneath the microscope lens using the controls (not shown) for manipulator 56. The operator searches for a class of fluid inclusions of interest, for example, the secondary inclusions along healed crack 36 in FIG. 1. Next, a single fluid inclusion of interest is identified. Feedthrough 66 is manipulated by rotation of shaft 68 until stylus 74 is above the identified fluid inclusion. Manipulator 56 may also be moved in order to position the slide relative to stylus 74.

When the feedthrough and slide are positioned as described above, shaft 68 is urged downwardly until diamond stylus 74 punctures the identified fluid inclusion thereby releasing gases and evaporated volatile liquids from the inclusion. It is to be appreciated that fluid inclusions may include mixtures of gases and liquids, and in some cases solids. Volatile liquids are those which evaporate when exposed to the vacuum within chamber 50.

When the inclusion is so ruptured, the gases released from the inclusion, including the evaporated volatile liquids, pass through tube 48 to ionization chamber 42 where the same are ionized. The ionized gases are accelerated in tube 40 toward magnet 46 which changes the direction of travel of the ionized gases.

Most fluid inclusions of interest in connection with exploration and production of oil and gas are water dominated. In water, the isotope ratios of most interest, and those which have the best chance of being analyzed, are $^{16}O/^{18}O$ $^1H/^2H$. These ratios can be determined by detecting the following ionic species: $H_2^{16}O+$, $HD^{16}O+$, and $H_2^{18}O+$.

The mass spectrometer is adjusted by adjusting the power of magnet 46 so that ionic species having a mass to charge ratio of 18, 19, and 20, namely $H_2^{16}O+$, $HD^{16}O+$, and $H_2^{18}O+$, strike end plate 87.

In FIG. 6, a first ion stream 92 is made up of $H_2^{16}O+$ ions, a second stream 94 is made up of $HD^{16}O+$ ions, and a third ion stream 96 is made up $H_2^{18}O+$ ions. Because each ion stream is made up of ions having a different mass-to-charge ratio, the effect of magnet 46 on the ions is to separate them into very slightly nonparallel streams of ions, each of which strikes end plate 87 in a predetermined location. It can, thus, be seen that by selectively positioning end plate 87 and electron multipliers 78, 80, an ion stream made up of ions having a selected mass-to-charge ratio may be directed into one of the electron multipliers while the other ions are absorbed in end plate 87. Each ion in, for example, ion stream 92, which passes through slit 88 and strikes electron multiplier 78 generates a shower of secondary electrons in multiplier 78 which is provided to ion counter 82. Each electron shower is counted by counter 82 as a single ionization event which is recorded by computer 86.

Detector 44 is advantageous when dealing with a very small gas sample, such as that which is released from a single fluid inclusion. Since electron multipliers do not necessarily release the same number of electrons in response to ions having the same mass-to-charge ratio, use of the ion counters to convert each electron shower into a single ionization event increases the accuracy of the collected data. It can be seen that by shifting end plate 87 and electron multipliers 78, 80 different selected ion streams may be detected. Furthermore, by changing the strength of the magnetic field generated by magnet 46, streams of ions having different mass-to-charge ratios than those shown in the example may be made to strike end plate 87 and/or pass through the slits therein.

Referring now to FIG. 5, in the operation of the embodiment shown therein, slide manipulator 56 is positioned until the fluid inclusion of interest is directly beneath diamond stylus 76. Thereafter, the controls (not shown) for manipulator 56 are operated to drive manipulator 56, and thus sample 10, directly upwardly into diamond stylus 76. Such ruptures the fluid inclusion positioned beneath the diamond stylus and permits the gases released therefrom to be analyzed, as described above. In operation of the embodiment of FIG. 5, an operator uses microscope 52 in the same manner as the embodiment of FIG. 4 to characterize a class of inclusions and to thereafter identify a particular inclusion for rupture in order to analyze the gases released therefrom.

Each diamond stylus 74, 76 includes a point sufficient to puncture fluid inclusions less than 10 microns in diameter.

It can thus be seen that the instant invention permits characterizing a class of fluid inclusions such as primary or secondary inclusions, for example, by observation (in the instant embodiment of the invention with an optical microscope) and thereafter identifying a single inclusion within the characterized class. The identified inclusion may then be ruptured and the gases released therefrom analyzed to derive information relating to the geologic process which formed the mineral containing the fluid inclusion.

The instant invention may, therefore, be used to verify whether or not prior art techniques for analyzing gases released from fluid inclusions, such as thermal decrepitation, are in fact sequentially and individually releasing gases from fluid inclusions, as is theorized by some. Moreover, the instant invention permits selecting a single particular identified fluid inclusion for rupturing in order to analyze gases released therefrom so that data from a particular characterized class of inclusions may be generated. Generating such data was not possible with the prior art techniques for releasing gases from fluid inclusions.

It is to be appreciated that additions and modifications may be made to the embodiments of the invention disclosed herein without departing from the spirit of the same which is defined in the following claims.

What is claimed is:

1. Apparatus for deriving information relating to the geologic processes which form naturally-occurring mineral, said apparatus comprising:

manipulating means for receiving and for manipulating a sample comprising a cut polished section of sedimentary rock containing a plurality of microscopic fluid inclusions of less than 50 microns in diameter, the fluid inclusions being of interest in the exploration for oil and gas;

microscope means for examining the sample as it is manipulated for characterizing a class of said microscopic fluid inclusions of less than 50 microns in diameter which are formed in such sample and for identifying and selecting in the sample a single microscopic fluid inclusion within said characterized class;

means comprising a stylus having a point smaller than the selected single microscopic fluid inclusion and effective for mechanically rupturing in the sample essentially only the identified and selected microscopic fluid inclusion of less than 50 microns in diameter while the sample is received by the manipulating means;

means connected between the sample and the analysis means for passing gases released from said fluid inclusion to the analyzing means; and means for analyzing gases passed from said fluid inclusion.

2. The apparatus of claim 1 wherein said means for analyzing the gases released from the inclusion comprises a mass spectrometer.

3. The apparatus of claim 2 wherein said mass spectrometer includes means for determining the isotropic ratios of selected elements in the gases.

4. THe apparatus of claim 2 wherein the means for analyzing comprises means for evaporating volatile liquids from the fluid inclusion.

5. The apparatus of claim 1 wherein the stylus has a point smaller than the selected single microscopic fluid inclusion and effective for mechanically puncturing in the sample essentially only an identified and selected fluid inclusion of less than 10 microns in diameter.

* * * * *